(12) United States Patent
Pierne

(10) Patent No.: US 12,390,616 B2
(45) Date of Patent: Aug. 19, 2025

(54) ACOUSTIC AND VISUAL ENERGY CONFIGURATION SYSTEMS AND METHODS

(71) Applicant: Dawn Ella Pierne, Naples, FL (US)

(72) Inventor: Dawn Ella Pierne, Naples, FL (US)

(*) Notice: Subject to any disclaimer, the term of this patent is extended or adjusted under 35 U.S.C. 154(b) by 641 days.

(21) Appl. No.: 17/220,376

(22) Filed: Apr. 1, 2021

(65) Prior Publication Data

US 2021/0308413 A1 Oct. 7, 2021

Related U.S. Application Data

(60) Provisional application No. 63/004,246, filed on Apr. 2, 2020.

(51) Int. Cl.
*A61M 21/02* (2006.01)
*A61M 21/00* (2006.01)

(52) U.S. Cl.
CPC ..... *A61M 21/02* (2013.01); *A61M 2021/0027* (2013.01); *A61M 2021/005* (2013.01); *A61M 2205/50* (2013.01); *A61M 2205/59* (2013.01)

(58) Field of Classification Search
CPC .......... A61M 21/02; A61M 2021/0027; A61M 2021/005; A61M 2205/50; A61M 2205/59; A61M 2021/0088; A61M 2205/505; G10H 1/0008; G10H 2210/471; G10H 2210/481; G10H 2210/576; G10H 2220/376; G10H 2250/395; G01N 37/005
USPC ...................................................... 600/26–28
See application file for complete search history.

(56) References Cited

U.S. PATENT DOCUMENTS

| | | | |
|---|---|---|---|
| 9,983,684 B2 | 5/2018 | Wang et al. | |
| 10,404,938 B1 | 9/2019 | DeBonoist et al. | |
| 2002/0128540 A1* | 9/2002 | Kim ...................... | G16H 15/00 |
| | | | 702/19 |

(Continued)

FOREIGN PATENT DOCUMENTS

| | | |
|---|---|---|
| ES | 2347517 A1 | 5/2011 |
| GB | 2567506 A | 4/2019 |

(Continued)

OTHER PUBLICATIONS

The Soul Medic by Dawn Ella, Sep. 18, 2015 (Year: 2015).*

(Continued)

*Primary Examiner* — Sunita Reddy
(74) *Attorney, Agent, or Firm* — Bochner PLLC; Thomas H Stanton

(57) ABSTRACT

The embodiment relates to systems and methods structured to deliver acoustic and visual energies to be received by living beings, and, more particularly the energies received by living beings can be configured, composed, and/or designed to be delivered to address a plurality of conditions including enjoyment. The energies can be deployed by using various algorithms and can include tones, tuning, rhythms, sound waves, harmonies, melodies, chord progression and instrument arrangement to deliver the energies preferentially to different parts of a living being's body, such as but not limited to, right and/or left ears. The algorithms can include variations in Pythagorean tuning and just and pure intonation, monaural and binaural beats for brain wave entrainment, Solfeggio Frequencies, Fibonacci Sequencing, and/or carrier waves and isochronic tones.

15 Claims, 7 Drawing Sheets

(56) References Cited

U.S. PATENT DOCUMENTS

| | | | |
|---|---|---|---|
| 2005/0215848 A1* | 9/2005 | Lorenzato | G04F 5/025 |
| | | | 600/27 |
| 2007/0135676 A1* | 6/2007 | How | A61M 21/0094 |
| | | | 600/26 |
| 2008/0071136 A1* | 3/2008 | Oohashi | G10H 7/00 |
| | | | 600/27 |
| 2010/0168504 A1* | 7/2010 | Castano, Sr. | A61M 21/0094 |
| | | | 600/27 |
| 2013/0071829 A1* | 3/2013 | Berezhkov | G09B 19/00 |
| | | | 600/27 |
| 2015/0351655 A1 | 12/2015 | Coleman | |
| 2016/0077547 A1 | 3/2016 | Aimone | |
| 2017/0188976 A1* | 7/2017 | Kalra | A61B 5/486 |
| 2017/0304585 A1 | 10/2017 | Goldberg et al. | |
| 2018/0117276 A1* | 5/2018 | Kantawala | A63H 3/003 |
| 2018/0133504 A1 | 5/2018 | Malchano | |
| 2019/0261080 A1 | 8/2019 | Gerber | |
| 2020/0282175 A1* | 9/2020 | Vitchoff | A61M 21/02 |
| 2021/0046276 A1* | 2/2021 | Papania | A61B 5/375 |

FOREIGN PATENT DOCUMENTS

| | | |
|---|---|---|
| WO | 2004087246 A1 | 10/2004 |
| WO | 2019036256 | 2/2019 |

OTHER PUBLICATIONS

Harvard Study on Meditation, https://news.harvard.edu/gazette/story/2011/01/eight-weeks-to-a-better-brain/.

Bio-Well Reference to Joules (measured by Bioelectrography), https://gdvusa.org/BioWell.pdf.

Bioelectrography https://www.iumab.org/bioelectrography/.

https://scholar.harvard.edu/sara_lazar.

\* cited by examiner

| Name | Fraction |
|------|----------|
| P1 | 1/1 |
| m2 | 15/14 |
| M2 | 8/7 |
| m3 | 6/5 |
| M3 | 5/4 |
| P4 | 4/3 |
| A4 | 7/5 |
| d5 | 10/7 |
| P5 | 3/2 |
| m6 | 8/5 |
| M6 | 5/3 |
| m7 | 7/4 |
| M7 | 15/8 |
| P8 | 2/1 |

Fig. 1

(PRIOR ART)

| Note | C | D | E | F | G | A | B | C |
|---|---|---|---|---|---|---|---|---|
| Ratio | 1/1 | 9/8 | 81/64 | 4/3 | 3/2 | 27/16 | 243/128 | 2/1 |
| Step | — | 9/8 | 9/8 | 256/243 | 9/8 | 9/8 | 9/8 | 256/243 | — |

Fig. 2

(PRIOR ART)

| | 1 | 2 | 4 | 8 | 16 | 32 | 64 | 128 | 256 | 512 | 1024 | 2048 | 4095 | 8192 | 16344 |
|---|---|---|---|---|---|---|---|---|---|---|---|---|---|---|---|
| C | | | | | | | | | | | | | | | |
| C#/Db | 1.067 | 2.134 | 4.271 | 8.543 | 17.09 | 34.172 | 68.344 | 136.69 | 273.375 | 546.75 | 1093.5 | 2187 | 4375 | 8748 | 19496 |
| D | 1.125 | 2.25 | 4.5 | 9 | 18 | 36 | 72 | 144 | 288 | 576 | 1152 | 2304 | 4608 | 9216 | 18432 |
| D3/Eb | 1.201 | 2.402 | 4.803 | 9.61 | 19.221 | 38.443 | 76.886 | 153.77 | 307.546 | 615.093 | 1230.18 | 2450.37 | 4920.75 | 9841.5 | 19681.4 |
| E | 1.265 | 2.53 | 5.06 | 10.125 | 20.25 | 40.5 | 81 | 162 | 324 | 648 | 1296 | 2592 | 5184 | 10368 | 20736 |
| F | 1.333 | 2.666 | 5.333 | 10.666 | 21.333 | 42.666 | 85.332 | 170.665 | 341.33 | 682.66 | 1365.22 | 2730.64 | 5461.88 | 10922.56 | 21845.12 |
| F#/Gb | 1.423 | 2.847 | 5.69 | 11.39 | 22.78 | 45.56 | 91.125 | 182.25 | 364.5 | 729 | 1458 | 2916 | 5832 | 11664 | 23328 |
| G | 1.5 | 3 | 6 | 12 | 24 | 48 | 96 | 192 | 384 | 768 | 1536 | 3072 | 6144 | 12288 | 24576 |
| G#/Ab | 1.601 | 3.203 | 6.407 | 12.814 | 25.629 | 51.258 | 102.515 | 205.03 | 410.06 | 820.125 | 1640.25 | 3280.5 | 6561 | 13122 | 26244 |
| A | 1.687 | 3.375 | 6.75 | 13.5 | 27 | 54 | 108 | 216 | 432 | 864 | 1728 | 3456 | 6912 | 13824 | 27648 |
| A#/Bb | 1.777 | 3.555 | 7.111 | 14.222 | 28.444 | 56.888 | 113.777 | 227.555 | 455.111 | 910.222 | 1820.44 | 3640.88 | 7281.77 | 14563.55 | 29127.1 |
| B | 1.898 | 3.796 | 7.59 | 15.187 | 30.375 | 60.75 | 121.5 | 243 | 486 | 972 | 1944 | 3888 | 7776 | 15552 | 31104 |

Fig. 3
(PRIOR ART)

ACOUSTIC AND VISUAL ENERGY CONFIGURATION SYSTEMS AND METHODS

BACKGROUND/SUMMARY

CROSS-REFERENCE TO RELATED APPLICATION

This application claims priority from U.S. Provisional Patent Application No. 63/004,246, filed Apr. 2, 2020, titled ACOUSTIC AND VISUAL ENERGY CONFIGURATION SYSTEMS AND METHODS which is hereby incorporated by reference herein for all purposes.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

Trademarks used in the disclosure of the invention and the applicants make no claim to any trademarks referenced.

BACKGROUND OF THE INVENTION

Field of the Invention

The embodiment relates to systems and methods structured to deliver acoustic and visual energies to be received by users, and, more particularly the energies received by users can be configured, composed, and/or designed to be delivered to address a plurality of conditions.

Description of Related Art

Meditation is a precise technique for resting the mind and attaining a state of consciousness that is totally different from the normal waking state. It is the means for fathoming all the levels of consciousness within an individual and experiencing the center of consciousness within.

Specifically, meditation can provide numerous physical and mental benefits. For example, on a physical level, meditation may increase a person's energy level, lower high blood pressure, improve the immune system, and reduce tension-based pain. On a mental level, meditation may, for example, decrease stress and anxiety, increase happiness, improve emotional stability, and achieve peace of mind. People who practice meditation regularly are more likely to experience these benefits.

The art of meditation has been divided into numerous techniques; however, four broad categories or meditative states encompass the majority of techniques: present moment awareness, transcendence, focused intention, and energized body-mind. All of these activate the relaxation response, but they trigger different regions of the brain and therefore have different effects on people.

Present moment awareness techniques focus on the present moment, on paying careful, close attention to everything happening while you meditate—the sensations in your body, the thoughts swimming in your mind, the noises you hear. With present moment awareness, you're observing as everything comes and goes in your awareness. Buddhist meditation practices such as Vipassana and Zen meditation fall into this category, as well as the popular mindfulness-based stress reduction (MBSR) program that offers secular, intensive mindfulness training to assist people with stress, anxiety, depression and pain.

The embodiment can also be incorporated into transcendence which are mantra-based meditations that take your mind to quieter levels of awareness into a transcendental state—where you go beyond the intellect and ego, beyond space, time and self—and gain a sense of universality or "oneness." Transcendental meditation and Primordial Sound Meditation are two types of meditation that fall into this category.

While meditating, the person practicing the embodiment of transcendental meditation sits in a comfortable position with eyes fixed on the video and silently listens to a sound mantra. A sound mantra is a sequence of notes formulated from ancient auditory schemes.

Typically, focused intention methods focus on the future, or bringing something about in the future, whether that be the perfect job, home, spouse, or feeling. Manifestation, creative visualization, prayer and hypnosis are examples of techniques that help you focus on a goal, a feeling, a future achievement—athletes use focused intention a lot. Imagine the basketball player visualizing himself being in the zone and scoring the winning point to help him get ready for a big game.

Many compassion meditations include, but are not limited to, loving-kindness, gratitude, and tonglen. These styles of meditation are configured for cultivating feelings that will help an individual in their everyday life.

Some active meditations include, an energized body mind and are configured to energize the mind and body and help you reach your peak performance state. In these meditations, your body is exerting effort, but your mind is totally calm. Some examples include Kundalini yoga and other strong breathwork practices, Vinyasa yoga, walking meditation, surfing, and running. The runner's high is a great example of the result of an active meditation.

The background of the techniques is important to define the practice of meditation for the novice.

Meditating outdoors in nature may facilitate improved meditation experiences compared to meditating indoors. Natural environments such as beaches, oceans, forests, waterfalls, and other pleasant settings can help people relax and focus while meditating. However, it may be impractical for people who do not live or work near these natural environments to meditate in natural environments. Virtual reality (VR), video and audio technology can let users view environments without incurring the need to travel for the experience. For example, the virtual environment may be a natural environment located across the world from the location of a user in real life. However, the outdoor and other experiences may not be readily available to everyone wanting to practice meditation.

BRIEF SUMMARY OF THE INVENTION

The embodiment in one form is directed to highly formulated visual, harmonic and melodic elements to invoke inflections of divine sparks of light derived from ancient auditory schemes, this harmonizing energy is measured in joules by a biometric wellness device and chakras and any other methods of measurement. The music is a highly formulated embodiment of harmonic and melodic sound elements through tones, tuning, rhythms, sound waves, harmonies and melodies used to harmonize vibrational energy that can be measured in Joules, among other methods of measurement. It is a method for promoting a higher meditative state. These states include transcendental meditation, among others, for a user using either a virtual reality environment, a visual or acoustic environment.

The embodiment provides for: a. systems and methods structured to deliver acoustic and visual energies to be received by users; b. energies received by users can be configured, composed, and/or designed to be delivered to address a plurality of conditions or enjoyment; c. energies can be deployed by using various algorithms and can include structuring pitch, tones, tuning, and frequency. Melodic Sound elements can include, rhythms, sound waves, harmonies and melodies to deliver the energies preferentially to different parts of a user's body such as but not limited to right and/or left ears; d. algorithms can include variations in Pythagorean tuning, just or pure intonation, monaural and binaural beats, isochronic tones for brain wave entrainment, Solfeggio Frequencies, Fibonacci Sequencing, and/or carrier waves; e. Users of the system/method include, but are not limited to, all individuals including medical professionals, mental health professionals, Federal and State Correctional Institutions, yoga professionals, and enlightened persons.

The instant invention provides music therapy through a form of meditation by means of implementing a computer-implemented method configured to establish an application on a server accessible to one or more users and emit one or more waves to facilitate brainwave entrainment in which various brainwave states may be experienced by a listener. In particular, the one or more waves are configured to stimulate the brain into entering a specific state of consciousness by using a pulsing sound to elicit the brain's frequency following response encouraging the brainwaves to align to the frequency of a given beat that can calm anxiety, reduce stress and ease pain. Binaural beats, for example, may be accessible to a user through the application and include auditory illusions perceived when two different pure-tone sine waves, both with frequencies lower than 1500 Hz, are presented to a listener with a slight frequency difference between them, typically less than 40 Hz. The brain perceives a third tone, which is the mathematical difference between the two frequencies. In implementations, binural beats in the theta waves range of about 4 Hz to about 8 Hz are associated with a deep relaxation, meditation, and creativity. In implementations, binural beats in the alpha wave range of about 9 Hz to about 13 Hz are associated with relaxation while a user is awake. In implementations, binural beats in the gamma wave range of about 40 Hz are associated with an increased mental activity such as perception, problem-solving, and consciousness. Monaural beats, binaural beats, and isochoric tones may be employed to induce desirable states of consciousness in the listener, establishing a conditioned reflex response to this altered vibrational state, thus imprinting a meditative state of consciousness.

The formulated embodiment utilizes conditioned reflex response exposing users to the inflections of divine sparks of light derived from ancient auditory schemes through the components of the soul link formulated embodiment. Consequently, the doorway to elevated consciousness will be awakened allowing for the rise of the individual's vibration and creation of new and more positive responses to the stimuli of the formulated embodiment: The mind is able to be programmed by this phenomenon where the brain sets up a series of responses based on exposure to past stimulants.

The embodiment in another form provides a virtual reality environment: visual or acoustic environment meditation system receives information from a user device of a user such as a smart phone, computer, tablet or specialized computer interface device running a software and applications to specifically transmit the medium experience desired by the user using a display, audio or VR system. The information used by the smart phone, computer. tablet or specialized computer interface device running a software and applications to specifically transmit the medium experience desired by the user includes a request for a meditation exercise, selections for the exercise and visually and auditory blend stimulation to promote the meditative experience. For instance, the user may select a type of meditation such as a meditation that focuses on breathing patterns or a meditation that involves a body scan of the user. Further, the user selects audio compilation/video location/electromagnetic frequency audio waves which are options of the meditation exercise. The location options include natural environments that are suitable for meditation such as a beach, a waterfall, and a forest. Based on the user's selections, the meditation system provides a meditation exercise and the visual and audio environment to the user's device of a user such as a smart phone, computer, tablet or specialized computer interface device running software and applications to specifically transmit the experience desired by the user. In particular, the meditation exercise includes either audio/video or textual instructions guiding the user through the experience. When the embodiment utilizes a VR environment the audio-visual component is presented to the user via a suitable VR device. The VR or visual environment can include images and photographs, videos or 360-degree imagery corresponding to the selected location for the meditation, for example, imagery of a beach, waterfall, or trees, to help provide an immersive environment for the user completing the meditation exercise. The VR or visual component can also be incorporated in a game or have gamification aspect to the VR system. The audio portion is designed to create visual elements and/or events in the VR environment synchronized with the meditation exercise.

The audio portion of the exercise is customized and can be created by the user, meditation professional or practitioner such that sounds of nature in each meditation will reflect the element with which the meditation is meant to transform.

There can be multiple elements in one meditation, such as mental being associated with air, physical being associated with the earth, spiritual being associated with fire, and emotional being associated with water.

Therefore, what is needed in the art is a system for the creation of visual, audio and VR recordings that provides the user with a visually-guided meditation that takes them through the outer and inner aspects of nature as they continue to move forward through a totally immersive experience, returning to the very point where they started in the beginning.

The invention in one form is directed to an audio-visual system where the audio and video information is designed and customized to correspond to the visual stimulus.

The embodiment in another form is directed to a sound formula where the composer utilizes a predetermined audio of a highly formulated embodiment of harmonic and melodic sound elements through tones, tuning, rhythms, sound waves, harmonies and melodies.

DESCRIPTION

BRIEF DESCRIPTION OF THE DRAWINGS

A further understanding of the nature and advantages of particular embodiments may be realized by reference to the remaining portions of the specification and the drawings, in which like reference numerals are used to refer to similar components. When reference is made to a reference numeral without specification to an existing sub-label, it is intended to refer to all such multiple similar components.

FIG. 1A table of the ratios of frequencies, using 7-limit Just Intonation;

FIG. 2 Pythagorean tuning method of musical tuning;

FIG. 3 A=432 concert pitch with Pythagorean Ratios in 15 Octaves;

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION

Figure 4:
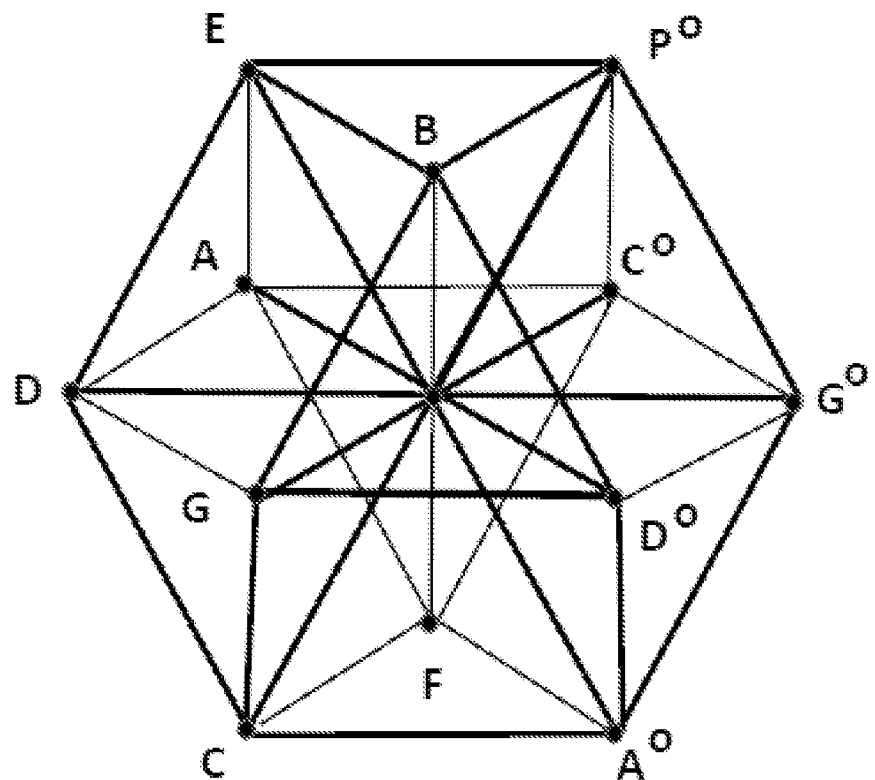
FIG. 4 Cuboctahedron chord progression relating to sacred geometry in sound.

As used within the specification, a user, a patient, an individual, a customer, an audience, a group, and/or a target means a person or group of persons who are desiring to engage in meditation.

As used within the specification, audio refers to sound, which is spoken sound, sung sound, musical instrument sound, sounds from nature, sounds made by animals, sounds made by machine and any live or recorded sound.

As used within the specification, visual or visual techniques refer to techniques including virtual reality, photographs, computer generated imagery (CGI), animation, motion graphics, videos and other video displays such as drone sequences (footage).

As used within the specification, visual display or visual playing refers to a means to reproduce a visual technique that is visible by a user such as a smart phone, computer, tablet or specialized computer interface device.

As used, the term composer, artist, videographer, musician, conductor, all refer to the individual responsible for using the video or audio formula to create the visual or audio component of the embodiment.

There are numerous prior art references that does not provide for an integrated system that provides synchronized audio and visual information using an audio formula and visual formula to create the audio and visual components of a meditation system.

Also, the prior art can provide insight into the meditation process.

The instant invention is a highly formulated embodiment of harmonic and melodic sound elements through tones, tuning, rhythms, sound waves, harmonies, melodies, chord progression and instrument arrangement meditation through binaural beats and visual stimuli rooted in quantum theory, sacred geometry, nature and epigenetics, for audiovisual human brain and nervous system's stimulation, restorative and therapeutic applications providing the user with a transcendental meditation experience or any other meditative states.

These energies received by users can be configured, composed and/or designed to be delivered to address a plurality of conditions or enjoyment. The instant invention is sure about the resilient power of sound and will educate and permeate music's healing properties for all mankind enhanced by the meditative and visual technologies that will make this tool transcendental for the user.

Through the formulated embodiment's algorithms structuring pitch, tone and frequency, the sound energies can be deployed preferentially to different parts of the user's body. Various individuals and organizations such as medical professionals, mental health professionals, federal and state correctional institutions, Yoga professionals and enlightened persons will all benefit from this technology. Each formulated embodiment includes all these aspects. The designer of the formulated embodiment must choose between Just or Pure Intonation or Pythagorean Tuning when tuning the sound.

Sound
   a. Tuning [0052] i. A=432 Hz—also known as "Verdi's A[0053] 1. Just or Pure Intonation [0054] 2. Pythagorean Tuning Harmony
   a. Cord Progression (sacred geometry)
   b. Solfeggio Frequencies
   c. Electromagnetic Frequency Audio Waves Melody
   a. The Fibonacci Sequence-Golden Ratio utilized in timing Sonatas
   b. Inflection of divine sparks of light derived from ancient auditory schemes Meditation & Consciousness
   a. Binaural beats for brainwave entrainment
   b. Transcendental meditation
   c. Conditioned reflex response Visual
   a. Quantum theory
   b. Sacred geometry
   c. Nature
   d. Epigenetics The instant invention formulated embodiment blend is not only auditory stimulation, but also stimulating through quantum theory and sacred geometry. The Weizmann Institute of Science states: "One of the most bizarre premises of quantum theory, which has long fascinated philosophers and physicists' alike states that by the very act of watching, the observer affects the observed reality." These researchers at the Weizmann Institute of Science conducted a highly controlled experiment demonstrating how a beam of electrons is affected by the act of being observed. The experiment revealed that the greater the amount of "watching" the greater the observer's influence on what actually takes place. The formulated embodiment takes advantage of this scientific principle when designing the visual component to positively affect the observer's reality and connect them with the sacred geometry in Nature. The instant invention provides visual imprinting through Quantum Theory into nature.

The instant invention produces experienced-based alterations in the brain and human consciousness through an innovative Meditation Formula of Sounds and Visuals. The instant invention improves emotion regulation and reduce anxiety symptoms, potentially improving the present-moment awareness, cultivating a healthy mind and increased well-being. Simply put, the instant invention is a unique transcendental meditative tool utilizing sound and audio to effectively change the brain structure of the user, thereby enhancing attention, yielding beneficial effects on physical, emotional, mental health and cognitive performance.

The user of the instant invention practices transcendental meditation by sitting in a comfortable position with eyes fixed on the visuals provided by the instant invention and silently listens to the instant invention formulated embodiment sound mantra melody. The instant invention sound mantra is a sequence of notes formulated from ancient auditory schemes.

Since transcendental meditation does not require strenuous effort, nor does it require concentration, or contemplation, the user can effortlessly obtain numerous benefits. Hari Sharma's research studies from the Center for Integrative Medicine, College of Medicine at The Ohio State University has found that "Meditation, as described in the ancient Vedic texts, is an exercise of consciousness that results in the expansion of consciousness beyond the day-to-day experience of duality. It is an experience of unity, which reduces stress and brings increased creativity and efficiency to the functioning of the inner faculty. This is a process that occurs without the mind directing the process. In physical exercise, the mind does not tell the muscles to get stronger; rather the muscles are strengthened automatically by the exercise process. Likewise, in this exercise of consciousness, that is meditation, the results are achieved automatically, not by controlling the mind or any other mental manipulation. The process of meditation goes beyond the mind to the deepest level of inner self.

The Mayo Clinic has identified high stress levels as one of the sources of many chronic health problems in our society such as high blood pressure, heart disease, obesity and diabetes. They suggest that Meditation is one of the tried and proven therapies to contribute towards the betterment of the health of the patient.

Extensive research from the most prestigious medical schools in the nation support the proven benefits of meditation in the medical field: Sarah Lazar of the MGH Psychiatric Neuroimaging Research Program is a Harvard Medical School Instructor in psychology states that "Although the practice of meditation is associated with a sense of peacefulness and physical relaxation, practitioners have long claimed that meditation also provides cognitive and psychological benefits that persist throughout the day". She also states that "her study demonstrated that changes in brain structures may underlie some of these reported improvements and that people are not just feeling better because they are spending time relaxing."

The instant invention is directed at an audio and visual system that is designed to promote the various meditative states as well as the transcendental meditation experience of a living being. The audio component is based on a sound formula which is utilized by the composers of the audio portion of the process to transport the listener to a state of mind that will create a higher order spiritual perspective. A critical component of meditation is the ability of the process to implement highly formulated harmonic and melodic elements to invoke inflections of divine sparks of light derived from ancient auditory schemes in the listener and raising vibrational energy by harmonizing vibrational energy measured in joules promoting various meditative states as well as a transcendental meditative state which can be measured in joules using the biometric wellness device or any other electronic methods that are suitable for measuring joules. The sound formula used in composing the music of the embodiment is structured to create a mechanism for transporting the listener to a sonic dimension that will create a new spiritual perspective. Therefore, the music needs to encourage introspection and the cultivation of inner truth. The embodiment utilizes a variety of stimuli such as sound and visual effects to transport the user to a higher dimension that will create a spiritual perspective. The resilient power of sound will accentuate the music's healing properties.

To achieve transportation of the user to a higher spiritual dimension the embodiment employs sound and video or visual stimulation to promote the meditative state. However, the sound must have the correct tuning to be effective. The embodiment incorporates specific tuning systems to stimulate the audience or user into desirable states of consciousness and ignite the healing properties of sound. The embodiment of the invention creates the embodiment sound formula based on harmonic and melodic sound elements through tones, tuning, rhythms, sound waves, harmonies, melodies, chord progression and instrument arrangement, to stimulate brain activity.

Referring now to the drawings, and more particularly to FIG. 1, there is shown a table of the ratios of frequencies, using 7-limit just intonation. Just intonation or pure intonation is the tuning of musical intervals as (small) small whole number ratios of frequencies. Just intonation, unlike standard 12-tone equal temperament, suggests many microtonally differentiated sizes of intervals, which stem from different regions of the harmonic series.

The 7-limit tuning is a system of just intonation where the frequency of each note is found by multiplying the frequency of a given reference note, by products of integer powers of 2, 3, 5 or 7. The boxes simply indicate more just ratios compared to 5-limit tuning.

Furthermore, one can envision just intonation tuning, also known as pure intonation tuning, which consists of microtonally differentiated sizes of intervals, stemming from different regions of the harmonic series. FIG. 1 shows the ratios of frequencies using 7-limit just intonation tuning, where the frequency of each note is found by multiplying the frequency of a given reference note by products of integer powers of 2, 3, 5, and 7.

The 432 Hz, Pythagorean Tuning is a system of musical tuning in which the frequency ratios of all intervals are based on the ratio 3:2. Referring to FIG. 2 which illustrates the 3:2 ratio of Pythagorean Tuning. The Pythagorean Tuning is when the frequency ratios of all intervals are based on the ratio 3:2, also known as the "Music of the Spheres." Mathematical relationships express qualities or "tones" of energy which manifest in numbers, visual angles, shapes and sounds, all connected within a pattern of proportion. Playing music using perfect ratios to increase brainwork integration facilitating the arrival to a pure state of consciousness.

Referring to FIG. 3 which illustrates A=432 Hz concert pitch with Pythagorean ratios in 15 octaves. The instant invention highly formulated embodiment's Sound blend can be tuned in A=432 Hz—also known as "Verdi's A." Additional aspects of tuning that are incorporated in this sound formula of the instant invention are Pythagorean tuning and just or pure intonation tuning.

When using Pythagorean Tuning all sonic properties should be tuned to "A" 432 Hz. This is accomplished on any software or physical instrument and is known as "Verdi's 'A'", and is based on 432 Hz and is mathematically consistent with the universe and was used in antiquity for various musical purposes, be them healing or celebratory.

Pythagoras believed that numbers were actually things that existed in a perfect, transcendent world beyond time, where perfect order always existed. He believed in a perfect platonic world of which ours was only an imperfect manifestation in time. This idea of a perfect other worldly order that is eternal and unchanging, of which our world is only an imperfect shadow, obviously had a massive influence on Christianity and Christian philosophy.

For Pythagoras, playing music using perfect ratios was not merely a way of creating beautiful music, but a way to tap into the divine, the transcendent; and to understand and experience the sublime and perfect order of true existence of which our temporal existence was only an imperfect shadow. In fact, this idea became so deeply entrenched in Christian and Western philosophy that over time a concept emerged called "Musica Universales", also known as "The Music of the Spheres."

This idea of "musica" does not mean what one would imagine when using the term "music." What it means is the proportions of the movements of the celestial bodies. In other words, the harmony at the basis of the entire universe, which had been prescribed by God in their mind, and so our human music was but an imperfect and temporal reflection of this order, of this "cosmic harmony." This idea had a very profound influence on the western school tradition and the emergence of its tradition of composers.

Either the Pythagorean or just or pure intonation methods of tuning may be used tuning the instrument of the embodiment.

Chord progression relating to the sacred geometry. The instant invention uses sacred geometry in all forms and can include many two and three dimensional configurations such as the cuboctahedron, cubes, pyramid, sphere, circle, equilateral triangle, pentagon, pentagram, hexagon, Egg of Life, Fruit of Life, Metatron's cube, Vesica Piscis, Seed of Life, Germ of Life, Tree of Life, Merkaba, Tetrahedron, Flower of Life and vector equilibrium. The next acoustical property used with the embodiment is that of harmony. Within the harmony property of the acoustic property of the embodiment is the concept of atmosphere. Atmosphere as used within the embodiment sound formula is aimed at creating a sonic dimension that embraces fluidity, motion and depth. The harmonic atmosphere is the blanket on which the melodic components lay, and as such, should need to be deep and slow. In the harmony, there are no sudden changes in character although the harmonic structure of any single meditation can evolve over time.

The next component of the embodiment sound formula is the concept of chord progression. Within the Chord progression is vector equilibrium which is one of the tools that is used within the embodiment harmony component of the sound formula where the chords are derived from the cuboctahedron shown in FIG. 4 which is known as the vector equilibrium. Chord progression relating to sacred geometry is used in the embodiment. One of the many sacred geometrical energy patterns that will be utilized is the vector equilibrium that is derived from the Cuboctahedron (sacred geometry). The vector equilibrium is an omnidirectional equilibrium of forces in which the magnitude of its harmonic potentials are exactly matched by the strength of its external cohering bonds.

This is the most primary geometric energy array in the cosmos, with all vectors being exactly the same length. The vector equilibrium is the ultimate and perfect condition wherein movement of energy comes to a state of absolute equilibrium yielding absolute stillness and nothingness. This chord progression will be the foundation of a number of the instant invention harmonic structures and facilitator for the various meditative states as well as transcendental meditation state.

According to Buckminster Fuller, the vector equilibrium is the most primary geometric energy array in the cosmos, with all vectors being exactly the same length. The vector equilibrium represents the ultimate and perfect condition wherein the movement of energy comes to a state of absolute equilibrium, and therefore absolute stillness and nothingness, and will be the foundation of some of the system of the invention harmonic structures. The chords will all consist of three notes generated from the triangular surfaces of the cuboctahedron. In sound, the cuboctahedron geometry refers to chord progression related to sacred geometry. The pulsing results in moving and expanding which flows into an octahedron and tetrahedron.

The patterns and ratios in nature are understood through sacred geometries. The living organisms of nature are the very essence of the DNA and Epigenetics, which does more than specify the structure and function of living things: it also serves as the primary unit of heredity in organisms of all types. That offspring reflects endlessness of The Creator contributing to the diversity of life.

The formulated embodiment of the Visual scenery in the meditation process allows the user to incorporate not only the outer aspects (external view) of the environment, but also the inner aspects (internal view) reflecting the true nature of our outer and inner world.

By allowing the user to take the visual journey down to the cellular level of the elemental kingdoms, sacred geometry amplifies connections to spirit, and creates harmony within the user's self, and between the user's self and the outside world. It can also be used to open up pathways to the infinite realms, as well as the connection to the oneness of all life, in nature and the whole world around us.

Figure 5:
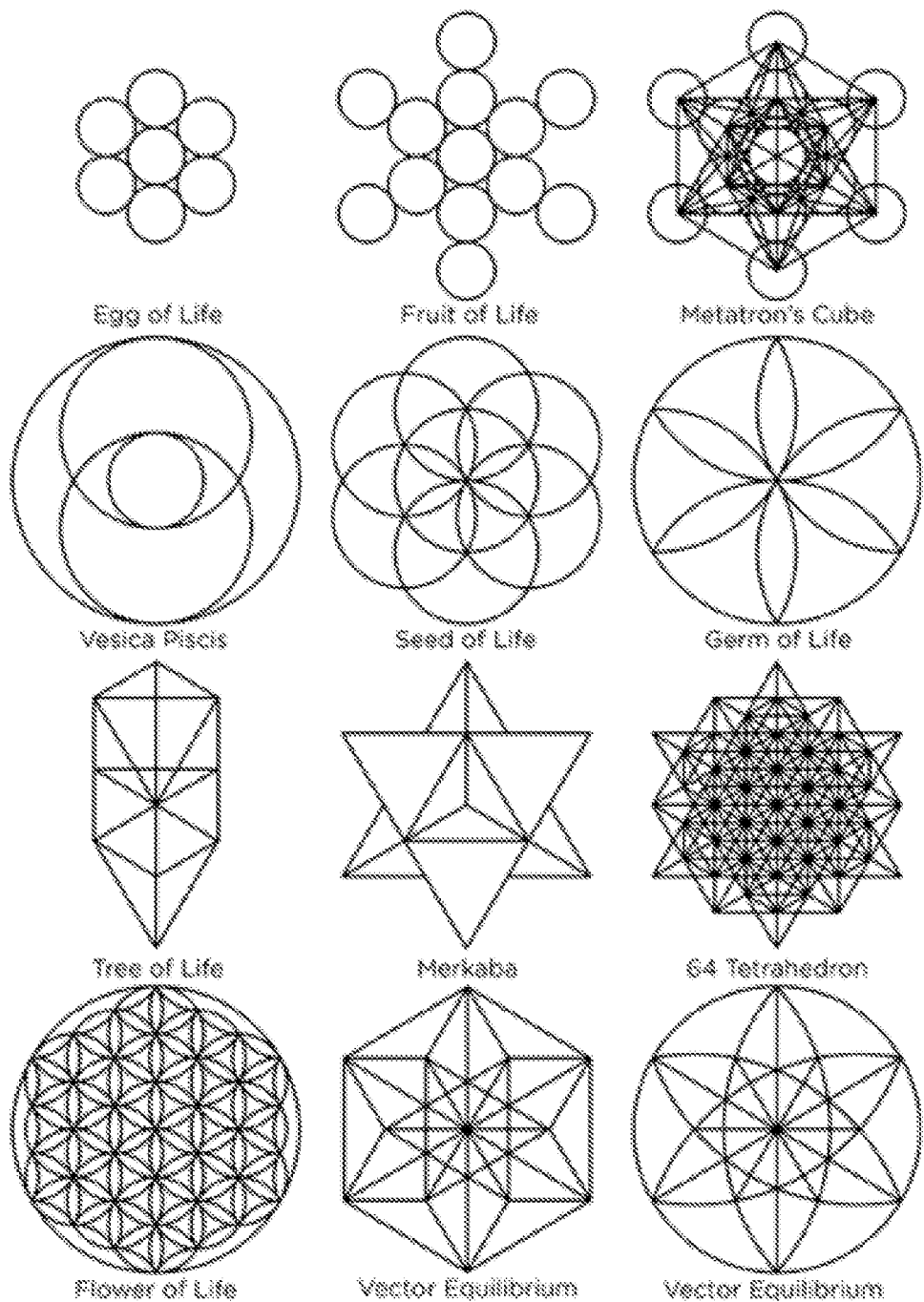
FIG. 5 Sacred geometry shapes.

As shown in FIG. 5 there are various sacred geometry shapes that will be incorporated and utilized in chord progression.

The instant invention formulated embodiment uses the principles of Epigenetics to better affect positive changes in the user's understanding of the influence of the environment on their DNA. Specifically, "Epigenetics is the study of how your behaviors and environment can cause changes that affect the way your genes work. Unlike genetic changes, epigenetic changes are reversible and do not change your DNA sequence, but they can change how your body reads a DNA sequence."

This environmental influence on how the body reads the DNA can yield positive or negative results in the users. "It is now widely accepted that epigenetic abnormalities contribute to the development and progression of human diseases, in particular cancers. Epigenetic processes are involved in the regulation in many events such a cell division, differentiation (specialization of cells in a particular role), survival, mobility. The alteration of these mechanisms promotes the transformation of healthy cells into cancer cells, any epigenetic aberration can be involved in carcinogenesis."

Epigenetic patterns may change throughout one's lifespan, by an early life experience, environmental exposure or nutritional status. Epigenetic signatures influenced by the environment may determine our appearance, behavior, stress response, disease susceptibility, and even longevity. The interaction between types of epigenetic modifications in response to environmental factors and how environmental cues affect epigenetic patterns will further elucidate how gene transcription can be affectively altered.

The instant invention has a formulated embodiment that uses the sacred geometry in Nature as the environmental cues to affectively and positively alter the gene transcription in order to reverse Epigenetic aberrations and restore the proper functioning of the user's genes.

All vectors in the cuboctahedron are equal in length, and the interval associated with the magnitude of each vector is an augmented fourth (tri-tone). The vector equilibrium sets up our harmonic principle. In each sound meditation, chords will have a tri-tonal relationship.

From the composer's point of view, one must choose a chord, any chord, built of three notes. The next chord is then revealed by finding the tri-tone of each of the original notes. For example: If the first chord is B-D #-G, the second chord will be F-A-C#. No key signature will be needed in invention, only this simple process of forming chords.

A critical part of the composition is how many pairs of chords to include in each meditation presentation to a user.

The next part of the embodiment sound formula is the arrangement of instruments or other musical producing devices. In implementations, the system uses monaural and binaural beats and isochoric tones for implementing brainwave entrainment. As noted above, brainwave entrainment is an assisted form of meditation using sound, light, and/or electromagnetic pulses to facilitate brain changes within its governing EEG frequency towards the frequency of a dominant auditory stimulus. It has been determined that any stable frequency evokes a cortical response. The brain synchronizes its dominant brainwave frequency with that of the external stimulus, which is typically referred to as brainwave entrainment. A preferred embodiment of the system utilizes brainwave entrainment which is a method to stimulate the brain into entering a specific state by using a pulsing sound, light, or electromagnetic field. The pulses elicit the brain's frequency following response, encouraging the brainwaves to align to the frequency of a given beat.

This frequency following response of brainwave entrainment can be seen in action with those prone to epilepsy. If a strobe flashes at their seizure frequency, the brain will 'entrain' to the flashing light, resulting in a seizure. However, a positive effect can be elicited from a user and used to induce many brainwave states: such as a trance, enhanced focus, relaxation, meditation or sleep induction. The brainwave entrainment effectively pushes the entire brain into a certain state.

Brainwave entrainment works for almost everyone. It is a way to lead your mind into states that you might usually have difficulty reaching, allowing you to experience what those states feel like.

The embodiment uses this technique to induce desirable states of consciousness in the listener, establishing a conditioned reflex response to this raised vibrational state measured in Joules and other methods of measurement. The system of the invention sonic properties includes waveforms at specific frequencies to usher in certain levels of consciousness, specifically:

Gamma State (38100 Hz, typically $^{-40}$ Hz)
Beta State (13-38 Hz)
Alpha State (9-13 Hz)
Theta State (4-8 Hz)

The instant invention formulated embodiment utilizes conditioned reflex response exposing users to the Inflections of divine sparks of light derived from ancient auditory schemes through the components of the instant invention formulated embodiment. Consequently, the doorway to elevated consciousness will be awakened allowing for the rise of the individual's vibration and creation of new and more positive responses to the stimuli of the formulated embodiment: The mind is able to be programmed by this phenomenon "where the brain sets up a series of responses based on exposure to past stimulants."

Desirable states of brain activity (i.e., alpha state, beta state, theta state) can be induced by exposing the brain to certain frequencies or visual stimuli.

The brain will move into the alpha state when exposed to an auditory stimulus with a mean pitch between 9 Hz and 13 Hz. Although this range of sound is far below the range of human hearing, alpha state can still be induced thanks to the brain's recognition of the difference of two tones sounded simultaneously through opposite ears (binaural beats).

Carrier Frequencies: If a tone at 432 Hz (carrier frequency 1) is sounded in one ear and a tone of 442 Hz (carrier frequency 2) is sounded in another, the difference is 10 Hz and the electrical brainwave pattern will resonate at 10 Hz.

Research has shown that people tend to entrain better to higher carrier frequencies than lower ones. However, what carrier frequencies lose in overall energy when decreased, they gain in capacity to resonate physical matter-including the brain-more forcefully.

The longer the exposure, the greater the payoff. Just like running for longer periods of time will eventually expand the capabilities of your lungs, heart & muscles to run longer in the future, so does greater exposure to certain brain states greatly influence the neurophysiology of the brain to better learn, strategize & communicate effectively in the future.

Therefore, within the embodiment the carrier frequencies can fluctuate in and out throughout a meditation of the invention to make the soundtrack more "listenable," but should be considered a critical building block. Note too, that binaural beats are only created when two sounds are sounded simultaneously. Cross-hemispheric communication in the brain is an integral part of the embodiment sound formula and this can only be achieved through the implementation of binaural beats.

The embodiment also incorporates the Solfeggio Frequencies into the sound formula. The Solfeggio Frequencies are reputed to be the original frequencies used by the Gregorian Monks when they chanted in meditation, and have long been thought to impart spiritual blessings, and are strategically implemented in the harmonic properties of the formulated embodiment based on the effect desired on the mind's consciousness.

The nine Solfeggio Frequencies and their effect on the consciousness of the mind:

174 Hz-Removal of Pain
285 Hz-Influence Energy Fields
396 Hz-Liberating Guilt and Fear
417 Hz-Undoing Situations and Facilitating Change
528 Hz-Transformation and Miracles (DNA Repair)
639 Hz-Relationships, Connecting with Spiritual Family
741 Hz-Expression/Solutions, Cleaning & Solving
852 Hz-Returning to Spiritual Order
963 Hz-Connection to the Cosmos; Awakening While these frequencies are commonly used, any desirable frequency can be used.

These nine frequencies should be strategically implemented in the harmonic properties of the embodiment sound formula or system, although not all at once.

Electromagnetic frequency audio waves will also aid in the instant invention formula given its ability to stimulate the human body to make chemical changes resulting in extraordinary cures for innumerable diseases.

The embodiment sound formula utilizes the electromagnetic frequency audio waves. Dr. Royal Rife invented a device which emitted audio waves that stimulated the human body to make chemical changes, resulting in extraordinary cures for innumerable diseases. The sound formula of the embodiment uses the same electromagnetic frequency combinations to raise a person's vibration. These frequency sets are documented on the electro therapy device frequency (ETDFL) and are incorporated into the sound formula.

Frequency sets are provided to the composer to ensure that they are incorporated correctly into the composition of the composer utilizing the embodiment.

As a rule, key frequencies need to be strategically implemented in the harmonic properties of the embodiment. This can be accomplished by the composer in post-production, where these frequencies can be "carved out" using equalization. However, the composer should specially consider them during the compositional stages.

The sound formula of the embodiment also benefits from the inclusion of natural sounds into the composition. Sounds found in nature should be added into the background elements of the composition used by the embodiment such as waves, forests, birds, waterfalls, wind chimes, etc.

Playing 'natural sounds' affects the bodily systems that control the flight-or-fight and rest-digest autonomic nervous systems, with associated effects in the resting activity of the brain.

Any instrument may be used when recording a composition to be used in the embodiment. It can be physical or software, symphonic or electronic. When live instruments are prescribed, it is best to record the live players to have an organic interpretation of the material.

The instant invention formulated embodiment makes use of a sequence of notes formulated from Inflections of divine sparks of light derived from ancient auditory schemes producing sound mantras allowing the mind to naturally transcend, while both the mind and the body remain awake, yet relaxed.

The instant invention uses music that works through rhythms since humans are rhythmic beings which is evidenced by the facts that our hearts beat, breathing and brain waves are all rhythmic. The human brain and nervous system are hard-wired to distinguish music from noise and to respond to rhythm and repetition, tones and tunes.

The Harvard Medical School Seminar "Music as Medicine" features an article by Dr. Anthony Komaroff in association with the Harvard Health Publications, in which he states: "Music seems to slow heart rates, lower blood pressure and reduce levels of stress hormones." Music can also provide relief to heart attack, stroke victims, patients undergoing surgery and provide a pleasant diversion during chemotherapy or a hospital stay by calming anxiety and easing pain. Research suggests that music may promote the brain's ability to make new connections between nerve cells and exert all these benefits. Music can awaken the brain and with it, the rich trove of memories that are associated with familiar songs or beloved pieces.

The Fibonacci Sequence has been nicknamed 'nature's code', 'the divine proportion', 'the golden ratio', 'Fibonacci's Spiral' amongst others. Simply put, it is a series of numbers: 0, 1, 1, 2, 3, 5, 8, 13, 21, 34, 55, 89, 144, 233, 377, 610 . . . . The next number in the sequence is found by adding up the two numbers before it. The ratio for this sequence is 1.618. This is what some people call 'The Divine Proportion', 'The Golden Ratio' or "Phi"" and is the method of composition for sound formulated embodiment of the instant invention.

Mozart, for instance, based many of his works on the Golden Ratio-especially his piano sonatas.

The traditional sonata has two parts: 1. Expositio—where the musical theme is introduced; 2. Development and recapitulatio—where the theme is developed and repeated.

Golden ratio utilized in timing Sonatas. Mozart arranged his piano sonatas so that the number of bars in the development and recapitulation divided by the number of bars in the exposition would equal approximately 1.618, the Golden ratio. At his point in the composition there was a definite change or climax, which is nicknamed the "Phi Moment" and may be found by taking the total number of beats, bars or seconds in a composition and multiplying it by 0.618. The sound and visual of the instant invention uses the Phi moment method for the compositions used in the formulated embodiment.

Phi moments may be found by taking the total number of beats, bars or seconds in a composition and multiplying it by 0.618.

The embodiment utilizes the Phi moment method in the compositions created for use in the embodiment. Although the notes of the melody will be provided, there should be a similar compositional layout as the above example from Mozart, where the individual parts of a movement, when divided, equal 1.618, the Golden Ratio. Parts can be identified either through melodic themes or the use of certain instruments.

To adequately create a composition that can be used in the embodiment the composer must utilize all of the elements and they need to be present in the composition used by the embodiment sound formula. The composition must have applicable tuning, harmony, chord progression, instrument arrangement, and/or melody to stimulate brain activity. However, a subset can be utilized by the system of the invention to achieve the desired effect. The selection of ingredients of the composition depends on the composer and their overall objectives.

The composition of the embodiment must be well mixed in order to be effective and stimulate results in brain activity but need to complement the embodiment stringent functional goals with musical beauty.

The embodiment also incorporates visual components into the system in a similar method to the audio process. The visual component is presented to the user at the same time as the choreography such that it is synchronized with the audio portion of the embodiment. The visual component is visually displayed or visually played which refers to a means to reproduce a visual technique that is visible by a user. The combination of the audio and visual increases the process of transporting the listener to a state of mind that will create a higher order spiritual perspective. The embodiment visual formula utilizes the incorporation of a variety of visual effects to assist in transporting the user to a high state of mind. Typical visual components of the immersion system of audio and visual is a visual formula including video-drone sequences (footage), CGI, Motion graphics and animation that are consistent with the transformational event of the meditation state achieved by using the embodiment. These visual formulas include: 360-Degree Drone Footage for Virtual Reality segments, Virtual Reality video streams which include scenes of nature and aerial landscapes, alluding to heightened consciousness and the unseen spiritual realm, photographs, videos, and other video displays. The Virtual Reality stream can be a well-choreographed slide show of videos and photographs can be substituted.

The visuals of the embodiment will be presented to create an interactive environment as Virtual Reality. Thus, aerial photographs and video can be used and are enhanced by using a 360-degree camera mounted on a drone or any other method suitable for the visual stream.

The instant invention also utilizes a visual imprinting method which utilizes special cinematic effect designed to draw the viewer into a visual landscape. This is known as infinite zoom cinematic techniques. This gives the viewer the sense of timelessness and endlessness which provides the ability to connect with the endlessness of the viewers soul. This feature includes scenes of nature and aerial landscapes including natural landscapes, water ebb and flow, plants, animals and any other visual art that reminds us of the principles of life and the universal connectedness of all things.

The instant invention allows one to provide views of nature which restores the balance and inner peace of the individual. The cinematic effect is the only means for viewers to tap into the sensation of endlessness.

The visual formula can utilize a video stream from a number of sources, including but not limited to animation, video, slide show, or any other type of video stream. For example, the invention or visual formula can incorporate 360-Degree Motion Graphics which allow the user to journey down to the cellular level of the elemental kingdoms, effectively recapturing our connection to our Soul's Divine Nature. The visual formula inner aspect can be created using CGI, Motion Graphics or animation and videos, such as drone sequences (footage) which can allow the user to perceive that they are imagining any aspect of the environment desired by the creator of the visual formula including going right up to and delving into the sun, tree or waterfall.

The embodiment is a visually guided transcendental meditation, or any other meditative state, which uses choreography of the visual and the audio portion, which is separately choreographed, to produce a seamless production. When the user takes the journey, it takes them through the outer and inner aspects of nature as they continue to move forward through a totally immersive experience, returning to the very point where they started in the beginning. This technique is known as "infinite zoom cinematic techniques".

The instant invention formulated embodiment provides views of nature which restores the balance and inner peace of the individual. In order to tap into the sensation of endlessness, the formulated embodiment utilizes the infinite zoom cinematic technique designed to draw the viewer into a visual landscape and finishing where they started. This gives the user the sense of timelessness and endlessness. This feature includes scenes of nature and aerial landscapes including natural landscapes, water ebb and flow, plants and animals and any other visual art that reminds us of the principles of life and the universal connectedness of all things.

An example is that the user imagines they are walking in an open field down a path filled with wildflowers; their pace increases and now you're running! Then, they take flight! Now their adventure is taking them flying towards the sun with a beautiful mountain landscape in the background. They are elevated even higher as you begin to see a broad perspective of the gorgeous landscape below. When they reach the mountain, and begin to climb each step of the mountain, they can feel themselves elevating higher and higher and higher. The sun is gleaming closer and closer to you as you reach the top of the mountain. The user is enveloped by an incredible elevated view.

Suddenly and miraculously, you see the rushing spray of a waterfall not too far from them and it draws their interest. Then they begin to navigate towards a spectacular waterfall in the near distance. As they draw closer to the waterfall, they gently fly in and through the beautiful downpour. The embodiment methodology creates this visual experience and integrates it with the synchronized audio composition of the sound formula produced by the composer.

The embodiment of the visual formula in the meditation process allows the user to incorporate not only the outer aspects (external view) of the environment, but also the inner aspects (internal view) reflecting the true nature of our outer and inner world.

The invention is unique in that the visual is not aligned and integrated with the sound, they are both separately choreographed pieces and the users have the ability to interchange them.

The combination of both audio and visual experience synchronizes to promote the meditative experience. The experience of going through the waterfall, as the user is going deep into the water allows them to immerse into the molecules themselves. At a deeply subconscious and spiritual level, the synchronized audio and visual allows the user to be drawn deep into their inner space. They are immersed within this elemental light, and the visuals become so clear that it begins to look as if they are soaring though the sky! Through this transition, they find themselves moving through puffy clouds high in the air. These clouds are full of color; painted in the most beautiful pastels.

As they start to descend, they sail over a turquoise lake of the most vivid color.

They arrive at the other side of the mountain, bringing them back over the top of the field of wildflowers where they started the journey. All the time, the audio portion of the invention is expanding the meditative experience. This journey has brought the user through many miraculous scenes, and at the final moments of the meditation, slowly descend, gently bringing them back to the Earth allowing them to ground their energy and absorb what they have experienced.

This and all meditations will always end back where they have started the journey. Once the user returns to where they started, the frame of movement stops. It is here that the visual landscape will slowly fade to white within a 10-second integration of time which can be 5, 10 or more seconds. Within a pre-determined time, which can be 5, 10 or more seconds the audio will fade to a harmonic resonance allowing the user to gradually descend to a normal functioning state of consciousness.

The embodiment integrates both the audio formula and the video formula to help the user achieve a higher meditative state. The use of the audio formula and the video formula promotes the higher meditative state.

The formulated embodiment with its highly formulated harmonic, melodic and visual elements harmonizes vibrational energies that can be measured in joules and other methods of measurement. It is a method for promoting a higher meditative state for a user in either a virtual reality environment or a visual/acoustic environment.

Figure 6:
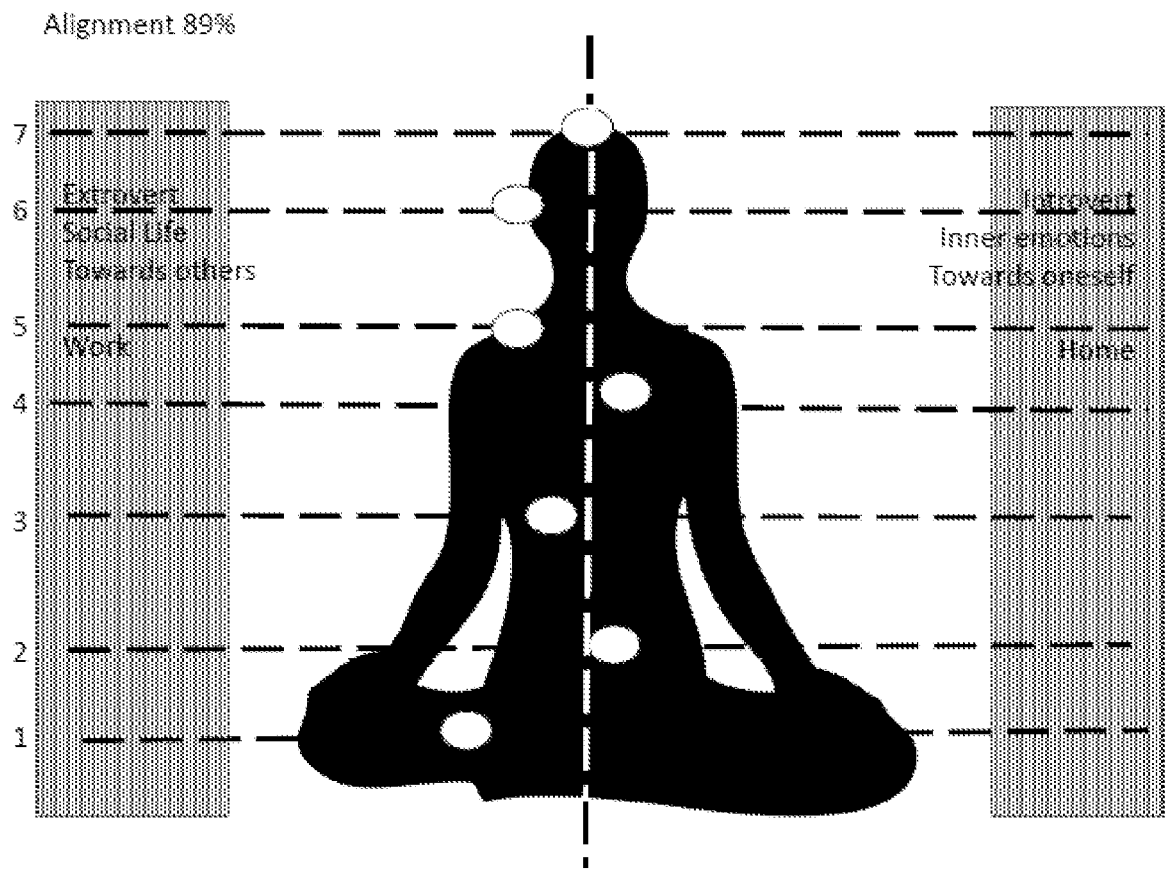
FIG. 6 Shows the change in alignment when an individual uses the instant invention at least 5 minutes per day for a week.
Figure 7:
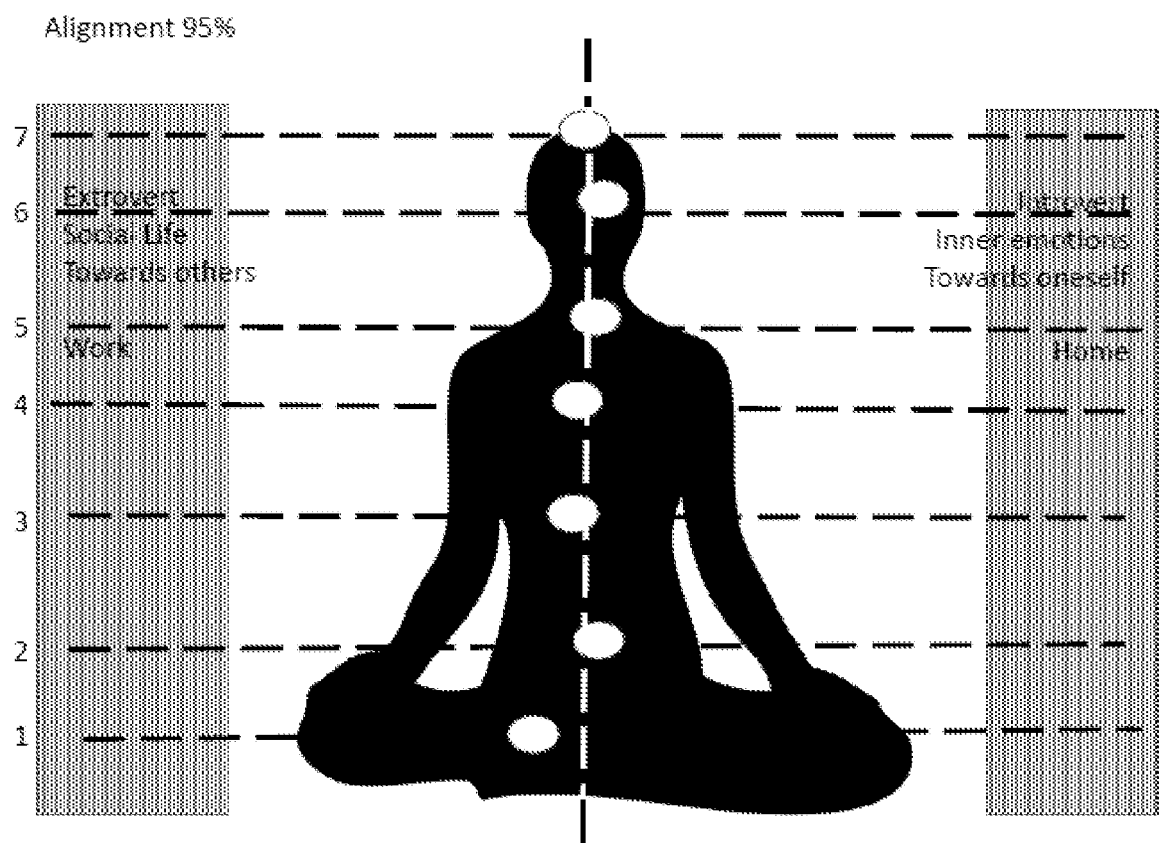
FIG. 7 Shows the change in alignment immediately after listening to the instant invention.

The positive effects measured by the biometric wellness device can be seen in FIG. 6 and FIG. 7 (Measured by Biolectography). https://gdvusa.org/BioWell.pdf and https://gdvusa.org/bio-well.html. FIG. 6 shows the change in alignment as an individual uses the instant invention at least 5 minutes per day for a week, and FIG. 7 shows the change in alignment immediately after listening to the instant invention.

The specification notes that transcendental meditation references include https://www.ncbi.nlm.nih.gov/pmc/articles/PMC4895748/and https://pubmed.ncbi.nlm.nih.gov/24626068/the contents of which are incorporated by reference in their entirety.

In some embodiments, the system, method or methods described above may be executed or carried out by a computing system including a tangible computer-readable storage medium, also described herein as a storage machine, that holds machine-readable instructions executable by a logic machine such as a processor or programmable control device to provide, implement, perform, and/or enact the methods described above, processes and/or tasks. When such methods and processes are implemented, the state of the storage machine may be changed to hold different data. For example, the storage machine may include memory devices such as various hard disk drives, CD, flash drives, cloud storage, or DVD devices. The logic machine may execute machine-readable instructions via one or more physical information and/or logic processing devices. For example, the logic machine may be configured to execute instructions to perform tasks for a computer program. The logic machine may include one or more processors to execute the machine-readable instructions. The computing system may include a display subsystem to display a graphical user interface (GUI) or any visual element of the methods or processes described above. For example, the display subsystem, storage machine, and logic machine may be integrated such that the above method may be executed while visual elements of the disclosed system and/or method are displayed on a display screen for user consumption. The computing system may include an input subsystem that receives user input. The input subsystem may be configured to connect to and receive input from devices such as a mouse, game controllers, video camera, camera, keyboard or gaming controller. For example, a user input may indicate a request that a certain task is to be executed by the computing system, such as requesting the computing system to display any of the information described above or requesting that the user input updates or modifies existing stored information for processing. A communication subsystem may allow the methods described above to be executed or provided over a computer network. For example, the communication subsystem may be configured to enable the computing system to communicate with a plurality of personal computing devices. The communication subsystem may include wired and/or wireless communication devices to facilitate networked communication. The described methods or processes may be executed, provided, or implemented for a user or one or more computing devices via a computer-program product such as via an application programming interface (API).

Since many modifications, variations, and changes in detail can be made to the described embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

In addition, the present invention has been described with reference to embodiments, it should be noted and understood that various modifications and variations can be crafted by those skilled in the art without departing from the scope and spirit of the invention. Accordingly, the foregoing disclosure should be interpreted as illustrative only and is not to be interpreted in a limiting sense. Further it is intended that any other embodiments of the present invention that result from any changes in application or method of use or operation, method of manufacture, shape, size, or materials which are not specified within the detailed written description or illustrations contained herein are considered within the scope of the present invention.

Insofar as the description above and the accompanying drawings disclose any additional subject matter that is not within the scope of the claims below, the inventions are not dedicated to the public and the right to file one or more applications to claim such additional inventions is reserved.

Although very narrow claims are presented herein, it should be recognized that the scope of this invention is much broader than presented by the claim. It is intended that broader claims will be submitted in an application that claims the benefit of priority from this application.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An electronic device configured to generate an audio input with one or more predetermined frequencies to stimulate brain activity to induce a brainwave state associated with a meditative state of consciousness, comprising:
    a display with a graphical user interface configured to emit a visual input;
    a tuning system configured to optimize an arrangement of a frequency of each note of a musical producing device with a sound formula based on the audio input having one or more harmonic and melodic sound elements; and
        wherein the tuning system is configured to tune the sound formula based on a 7-limit just intonation, where a frequency of notes of the one or more sound elements is derived from a base frequency of a reference note multiplied by products of integer powers of 2, 3, 5, and 7, and
        wherein the 7-limit just intonation includes microtonally differentiated sizes of intervals from different regions of a harmonic series;
    one or more speakers of the electronic device configured to emit a first tone of the notes of the one or more sound elements, based on the sound formula; and
        wherein the one or more speakers of the electronic device is configured to emit a second tone of the notes of the one or more sound elements, based on the sound formula; and
        wherein a difference between the first tone and the second tone has a beat frequency, wherein the beat frequency includes-being the one or more predetermined frequencies;
        wherein the one or more predetermined frequencies are selected from the group consisting of Gamma State (38-100 Hz), Beta State (13-38 Hz), Alpha State (9-13 Hz) and Theta State (4-8 Hz); wherein stimulating the brain activity to induce the brainwave state associated with the meditative state of consciousness includes the user brain wave entrainment to the selected predetermined frequency.

2. The electronic device of claim 1, further comprising: processing the visual input with one or more visual techniques, said one or more visual techniques are selected from the group consisting of virtual reality, photographs, videos, computer generated imagery, motion graphics, animation, drone sequences and 360-degree drone sequences.

3. The electronic device of claim 2, wherein said one or more visual techniques utilize infinite zoom visual techniques.

4. The electronic device of claim 3, wherein said infinite zoom visual techniques are selected from the group consisting of nature scenes and aerial landscapes, natural landscapes, water ebb and flow, plants and animals and visual art.

5. The electronic device of claim 1, further comprising:
one or more audio algorithms selected from the group consisting of Pythagorean tuning, isochronic tones, Solfeggio frequencies, Fibonacci sequencing, and electromagnetic frequency audio waves,
wherein the one or more audio algorithms being implemented into the sound formula.

6. The electronic device of claim 1, wherein said audio input has sonic properties comprising waveforms tuned to the one or more predetermined frequencies.

7. The electronic device of claim 1, further comprising:
implementing one or more chord progressions implemented into the sound formula, wherein the one or more chord progressions are selected from the group consisting of cuboctahedron, cubes, pyramid, sphere, circle, equilateral triangle, pentagon, pentagram, hexagon, Egg of Life, Fruit of Life, Metatron's cube, Vesica Piscis, Seed of Life, Germ of Life, Tree of Life, Merkaba, 64 Tetrahedron, Flower of Life and Vector Equilibrium.

8. A method for promoting a transcendental meditative state of a user through a use of visual and audio input forming a medium experience, wherein said medium experience comprises
a transcendental meditation system having a virtual reality environment and said virtual reality environment projecting the visual input and the audio input to the user and said meditation system receives information from a computerized device; and
wherein
the computerized device is configured to generate the audio input with one or more predetermined frequencies to stimulate brain activity to induce a brainwave state associated with the transcendental meditative state of the user, including:
a display with a graphical user interface configured to emit a visual input; and
a tuning system configured to optimize a frequency of each note of a musical producing device with a sound formula based on the audio input having one or more harmonic and melodic sound elements; and
wherein the tuning system is configured to tune the sound formula based on a chord progression, where a vector equilibrium is based on three-note chords derived from triangular surfaces of a cuboctahedron, and
wherein the vector equilibrium is an omnidirectional equilibrium of forces in which a magnitude of harmonic potentials of the vector equilibrium are equal to a strength of external cohering bonds of the vector equilibrium;
one or more speakers of the computerized device configured to emit the audio input at the one or more predetermined frequencies;
wherein the one or more predetermined frequencies are selected from the group consisting of Gamma State (38-100 Hertz (Hz)), Beta State (13-38 Hz), Alpha State (9-13 Hz) and Theta State (4-8 Hz); wherein the promoting the transcendental meditative state of the user through the use of visual and audio input forming the medium experience includes the user brain wave entrainment to the selected predetermined frequency.

9. The method of claim 8, wherein said computerized device is selected from the group consisting of a smart phone, a computer, a tablet or specialized computer interface device running a software and applications to specifically transmit a medium experience desired by the user using a display or audio system.

10. The method of claim 8, wherein the medium experience includes visually and auditory blend stimulation exercise and visually and auditory blend stimulation.

11. A computer-implemented method for promoting a meditative state of a user with synchronized visual input and audio input based on a sound formula forming a medium experience, the method comprising:
establishing an application on a server accessible to the user from a computerized device;
responsive to a request for the medium experience by the user, displaying the visual input from a display of the computerized device;
generating the sound formula based on one or more sound elements stored in computer readable memory and associated with the medium experience;
tuning, using a tuning system, a frequency of the audio input to one or more predetermined frequencies based on the sound formula using Pythagorean tuning with a base frequency of 432 Hertz (Hz), wherein a frequency ratio of an interval is based on a ratio of 3:2, and
wherein the tuning system is configured to optimize an arrangement of a frequency of each note of a musical producing device with the sound formula based on the audio input having one or more harmonic and melodic sound elements; and
wherein the interval is a difference in pitch between two notes of the one or more sound elements;
emitting, from a speaker of the computerized device, the one or more predetermined frequencies to stimulate brain activity to induce a brainwave state associated with the meditative state of the user;
wherein the one or more predetermined frequencies are selected from the group consisting of Gamma State (38-100 Hz), Beta State (13-38 Hz), Alpha State (9-13 Hz) and Theta State (4-8 Hz); wherein the promoting the transcendental meditative state of the user through the use of visual and audio input forming the medium experience includes the user brain wave entrainment to the selected predetermined frequency.

12. The computer-implemented method of claim 11, wherein the one or more sound elements include raising vibrational harmonizing by harmonized vibrational energy promoting the meditative state.

13. The computer-implemented method of claim 12, wherein said vibrational harmonizing by the harmonized vibrational energy is measured in joules using the computerized device.

14. The computer-implemented method of claim 11, wherein the display of the computerized device is implemented in a virtual reality environment.

15. The computer-implemented method of claim 14, wherein said computerized device is selected from the group consisting of a smart phone, a computer, a tablet or specialized computer interface device running a software and applications.

* * * * *